United States Patent [19]

Serban et al.

[11] Patent Number: 4,460,588

[45] Date of Patent: Jul. 17, 1984

[54] 5-SUBSTITUTED PYRIMIDINE DERIVATIVES ACTIVE AGAINST INTERNAL ANIMAL PARASITES

[75] Inventors: Alexander Serban, Doncaster; Keith G. Watson, Box Hill North; Colin Wilshire, East Doncaster; Bruce A. Forsyth, Croydon, all of Australia

[73] Assignee: ICI Australia Limited, Melbourne, Australia

[21] Appl. No.: 119,006

[22] Filed: Feb. 5, 1980

[30] Foreign Application Priority Data

Feb. 16, 1979 [AU] Australia ............... PD7721
Aug. 29, 1979 [AU] Australia ............... PE0244
Sep. 27, 1979 [AU] Australia ............... PE0672

[51] Int. Cl.³ ............... A61K 31/505; C07D 239/34
[52] U.S. Cl. ............... 424/251; 544/298; 544/301; 544/311; 544/312; 544/316; 544/318; 544/319; 544/321
[58] Field of Search ............... 544/315, 298, 316, 318, 544/251; 424/251

[56] References Cited

U.S. PATENT DOCUMENTS 3,896,235 7/1975 Harfeinst ............... 424/324
4,001,234 1/1977 Johnston ............... 260/256.4 C

FOREIGN PATENT DOCUMENTS 0001187 3/1979 European Pat. Off. .
1670695 12/1970 Fed. Rep. of Germany .
109170 10/1974 Fed. Rep. of Germany .
1486930 5/1967 France .

OTHER PUBLICATIONS

Frosyth, et al., "Chemical Abstracts", vol. 94, col. 94:103414h, 1981.
"Arzneimittel", Band 5, Teil, 2, 1972, pp. 37,98,99,109,190,191.
Kijima, et al., "Chemical Abstracts", vol. 93, col. 150268c.
Jojima, et al., "Agr. Biol. Chem.", vol. 30, No. 9, 1966, pp. 896-905.

Primary Examiner—Donald G. Daus
Assistant Examiner—James H. Turnipseed
Attorney, Agent, or Firm—Cushman, Darby & Cushman

[57] ABSTRACT

The invention concerns a process for killing internal parasites, especially trematodes or nematodes, affecting warm blooded animals such as cattle, sheep and goats by administering an effective amount of a composition containing as active ingredient a compound of the formula

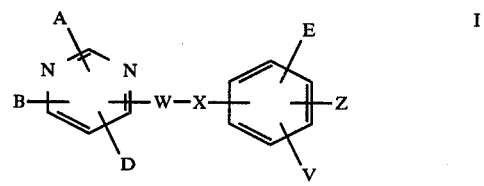

Certain of the compounds of formula I are novel and in further embodiments the invention provides novel compounds and compositions for use in the process of the invention. The process of the invention is especially applicable to the tretment of warm blooded animals infected with the trematodes Fasciola hepatica (liver fluke).

16 Claims, No Drawings

5-SUBSTITUTED PYRIMIDINE DERIVATIVES ACTIVE AGAINST INTERNAL ANIMAL PARASITES

This invention relates to processes for killing internal parasites of warm blooded animals by the administration of certain aromatic ether derivatives, to compositions for killing internal parasites of warm blooded animals; and to novel aromatic ether derivatives. In particular the invention relates to processes, compositions and compounds for killing trematodes or nematodes.

An example of a trematode is the liver fluke (*Fasciola hepatica*) which is a parasite of bile ducts of the liver of ruminants, such as cattle, sheep and goats. The liver fluke each year causes a significant amount of economic loss, not only from the death of the host animal but also from the deterioration in the value of meat and wool produced by infected animals. In cattle a loss in milk yield from liver fluke infection will also occur and in addition the loss sustained by the condemnation of infected livers as human food may also be considerable. An example of a nematode is *Haemonchus contortus* which is a nematode parasitic in the abomasum or fourth stomach of ruminants. It is a blood sucking parasite and when present in large numbers can cause anaemia and finally the death of the host. It can cause extensive losses, not only in the value of the animals which it may kill but also in the diminished production of commercial items such as wool and meat. There is therefore a commercial need to treat animals with chemicals which are both safe and effective in reducing the incidence and severity of diseases caused by both trematodes and nematodes.

Accordingly we provide a process for killing internal parasites of warm blooded animals which process comprises treating the infected animal with an effective amount of a composition comprising as active ingredient a compound of the formula I:

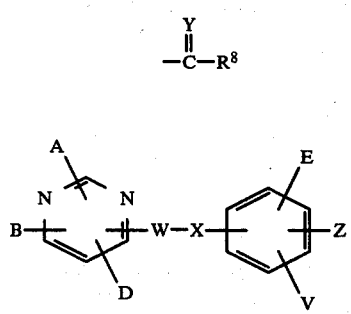

wherein

W is the group $-Z_m-(CR^1R^2)_n-(CHR^3)_p-\{O-(CHR^4)_q-(CHR^5)_r\}_s-$ in which Z is oxygen or sulfur, $R^1$, $R^2$, $R^3$, $R^4$ and $R^5$ are independently chosen from hydrogen and lower alkyl, m is 0 or 1, n, p, q, r and s are independently 0 or an integer from 1 to 6, provided that m is 0 when n and p are both 0, s is 0 when q and r are both 0, and $n+p+s(q+r)$ is not greater than 12;

A, B, D, E and V are independently chosen from the group consisting of hydrogen, halogen, nitro, amino, cyano, hydroxy, mercapto, thiocyano, carboxy, formyl, lower alkanoyl, (lower alkoxy)carbonyl, optionally substituted lower alkyl, optionally substituted lower alkoxy, optionally substituted lower alkenyl, optionally substituted aryl, optionally substituted aryloxy, optionally substituted lower alkythio, lower alkanoylamino, lower alkylamino and lower di(lower alkyl)amino; Z is chosen from isothiocyanate and $NR^6R^7$ wherein $R^6$ is chosen from hydrogen and lower alkyl and $R^7$ is chosen from hydrogen, optionally substituted lower alkyl, optionally subsituted lower alkenyl and the group

in which Y is oxygen or sulfur and $R^8$ is optionally substituted lower alkyl or optionally substituted lower alkenyl, provided that Z is not isothiocyanate when A, B, D, E and V are chosen from amino, hydroxy, mercapto, thiocyano, carboxy, lower alkanoylamino, and lower alkylamino; and X is oxygen or sulfur; or a salt thereof; and a carrier therefor.

By lower alkyl and lower alkoxy we mean a group containing from one to six carbon atoms, and by lower alkenyl and alkanoyl we mean a group containing from two to six carbon atoms.

When, in the process of the invention, one or more of A, B, D, E, V, $R^7$ and $R^8$ in the compound of formula I is substituted lower alkyl or substituted lower alkenyl or one or more of A, B, D, E and V is substituted lower alkoxy or substituted lower alkylthio, suitable substituents include, for example, one or more halogen atoms, or lower alkoxy or optionally substituted aryl groups.

When in the process of the invention, one or more of A, B, D, E and V in the compound of formula I is optionally substituted aryloxy, suitable aryloxy include, for example, phenyl optionally substituted with one or more atoms or groups chosen from halogen, lower alkyl, lower alkoxy, nitro and cyano.

When in the process of the invention, one or more of A, B, D, E and V or an optional substituent of a lower alkyl, lower alkoxy, lower alkylthio or lower alkenyl group in the compound of formula I is optionally substituted aryl suitable aryl include, for example, phenyl optionally substituted with one or more atoms or groups chosen from halogen, lower alkyl, lower alkoxy, nitro and cyano.

When one or more of A, B, D, E and V is chosen from hydroxy, mercapto or carboxy the compounds of formula I may be used in the process of the invention in derivative form, conveniently as a salt of a pharmaceutically acceptable inorganic or organic base. Suitable bases include, for example, pharmaceutically acceptable alkali metal hydroxides, alkaline earth metal hydroxides and amines such as ammonia, triethanolamine and N-methylglucamine.

When one or more of A, B, D, E and V is chosen from amino, lower alkylamino or di(lower alkyl)amino or $R^7$ is hydrogen, lower alkyl or lower alkenyl the compounds of formula I may be used in the process of the invention in derivative form, conveniently as the salt of a pharmaceutically acceptable inorganic or organic acid. Suitable acids include, for example, pharmaceutically acceptable acids chosen from hydrochloric acid, hydrobromic acid, sulfuric acid, phosphoric acid, nitric acid, maleic acid, acetic acid, benzoic acid, succinic acid, malic acid and ascorbic acid.

Suitable A, B, D, E and V include hydrogen, halogen, nitro, amino, cyano, hydroxy, mercapto, thiocyano, carboxy, formyl, $C_2$ to $C_6$ alkanoyl, ($C_1$ to $C_6$ alkoxy)carbonyl, $C_2$ to $C_6$ acylamino, $C_1$ to $C_6$ alkylamino, di($C_1$ to $C_6$ alkyl)amino, the groups phenyl and phenoxy each optionally substituted with one or more atoms or groups chosen from halogen, $C_1$ to $C_6$ alkyl, $C_1$ to $C_6$ alkoxy, nitro and cyano, and the groups $C_1$ to $C_6$ alkyl, $C_1$ to $C_6$ alkoxy, $C_2$ to $C_6$ alkenyl and $C_1$ to $C_6$ alkylthio each optionally substituted with one or more atoms or groups chosen from halogen, $C_1$ to $C_6$ alkoxy and phenyl.

Suitable $R^1$, $R^2$, $R^3$, $R^4$, $R^5$ and $R^6$ include hydrogen and $C_1$ to $C_6$ alkyl.

Suitable $R^7$ include hydrogen and the groups $C_1$ to $C_6$ alkyl, $C_2$ to $C_6$ alkenyl, $C_2$ to $C_6$ alkanoyl, $C_2$ to $C_6$ alkylthiocarbonyl, $C_3$ to $C_6$ alkenoyl and $C_3$ to $C_6$ alkenylthiocarbonyl each optionally substituted with one or more atoms or groups chosen from halogen, $C_1$ to $C_6$ alkoxy and phenyl.

Preferred A, B, D, E and V include hydrogen, halogen, $C_1$ to $C_6$ alkyl optionally substituted with one or more halogen atoms, nitro, cyano, hydroxy and $C_1$ to $C_6$ alkoxy.

Preferred $R^1$, $R^3$, $R^4$ and $R^5$ include hydrogen and methyl. Preferred $R^2$ is hydrogen.

Preferred z includes isothiocyano and $NHR^7$ wherein $R^7$ is selected from hydrogen, $C_2$ to $C_6$ alkanoyl and $C_3$ to $C_6$ alkenoyl.

Preferred X and Z are oxygen.

Preferred compounds for use in the process of the invention include:

(a) those compounds in which the pyrimidyl ring is substituted in the 2-position by the group

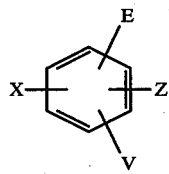

that is, compounds of formula II (I wherein in the group W, m, n, p and s are all 0) wherein A, B, D, E, V, Z and X are as hereinbefore defined.

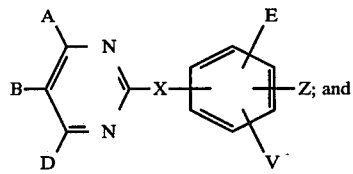

(b) those compounds in which the pyrimidyl ring is substituted in the 2-position by the group

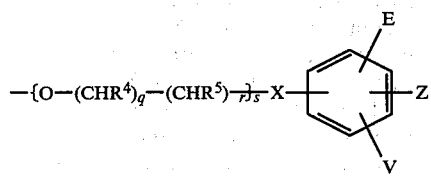

that is, compounds of formula III (I wherein the group W, m, n and p are all O) wherein A, B, D, E, V, X, $R^4$, $R^5$, Z, q, r and s are as hereinbefore defined.

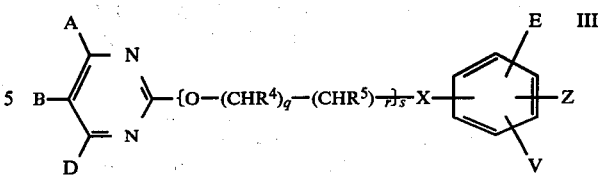

Examples of compounds which may be used in the process of the invention include:

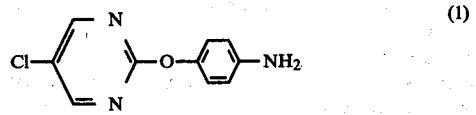
(1)

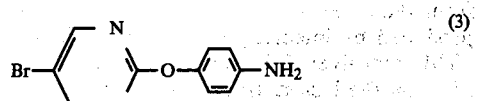
(3)

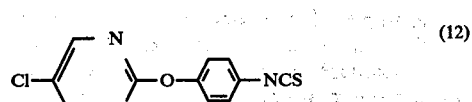
(12)

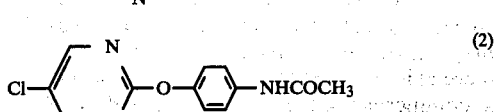
(2)

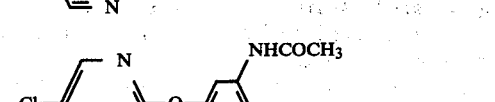

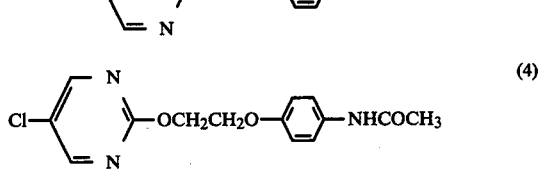
(4)

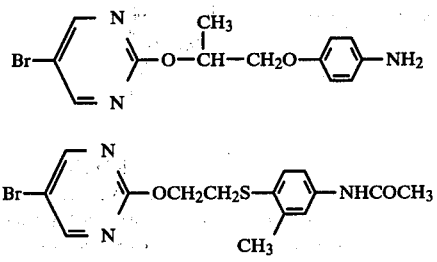

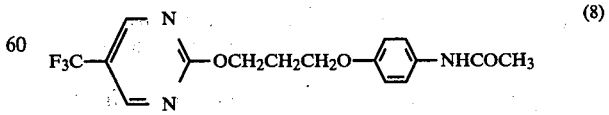
(8)

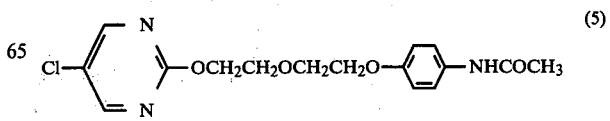
(5)

-continued

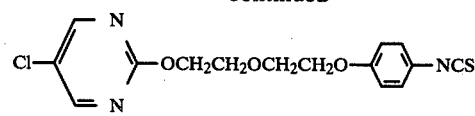

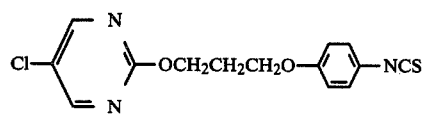

(7)
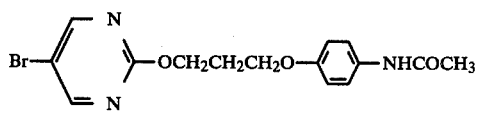

(11)
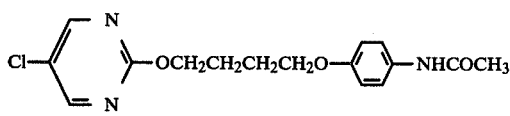

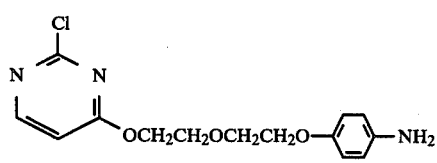

The compounds of formula I which may be used in the process of the invention may be prepared by a number of methods. Conveniently compounds of formula I wherein the group

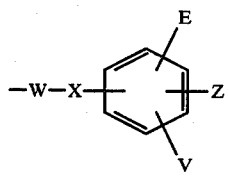

is substituted into the 2- or 4- position of the pyrimidyl ring, that is compounds or formula IV and V respectively IV
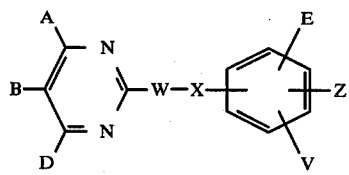

V
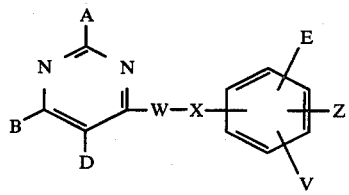

wherein A, B, D, E, V, W, X and F are as hereinbefore defined and in the group W m is 1, or m, n and p are all 0, or m, n, p and s are all zero, may be prepared by the reaction of a pyrimidine derivative of formula X, wherein L is a leaving group (eg Cl, Br, I or alkylsulfonyl) with a compound of formula XI, preferably in the presence of a basic material; according to SCHEME 1.

SCHEME 1

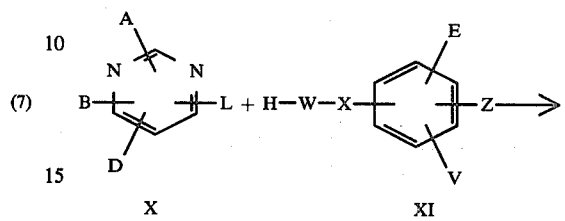

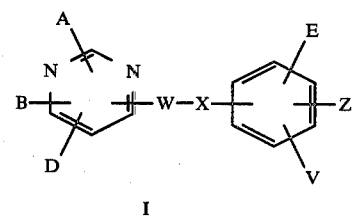

Alternatively, compounds of formula I wherein the group

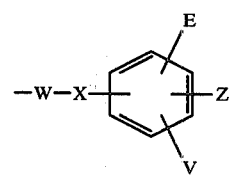

is substituted into the 2- or 4- positions of the pyrimidyl ring, that is compounds of formula IV and V respectively wherein A, B, D, E, V, W, X and Z are as hereinbefore defined and in the group W m is 1, or m, n and p are all zero, or m, n, p and s are all zero, may be prepared by the following steps in sequence; and p are all zero, or m, n, p and s are all zero, may be prepared by the following steps in sequence.

(a) reaction of a pyrimidine derivative of formula X wherein L is a leaving group (eg Cl, Br, I or alkylsulfonyl) with a compound of formula XII, preferably in the presence of a basic material, to give an ether or thioether of formula XIII;

(b) reduction of the nitro group in the compound of formula XIII (eg using iron and acetic acid) to give an amine of formula XIV which is the compound of formula I wherein Z is amino. (SCHEME 2).

The compounds of formula I wherein Z is thiocyano may be prepared from the compounds of formula XIV by the known prior art methods for conversion of an amino group to an isothiocyano group, for example by reaction with thiophosgene. (SCHEME 2, step c).

The compounds of formula I wherein Z is $NR^6R^7$ may be prepared by acylating or alkylating the amine of formula XIV. (SCHEME 2, step d).

SCHEME 2

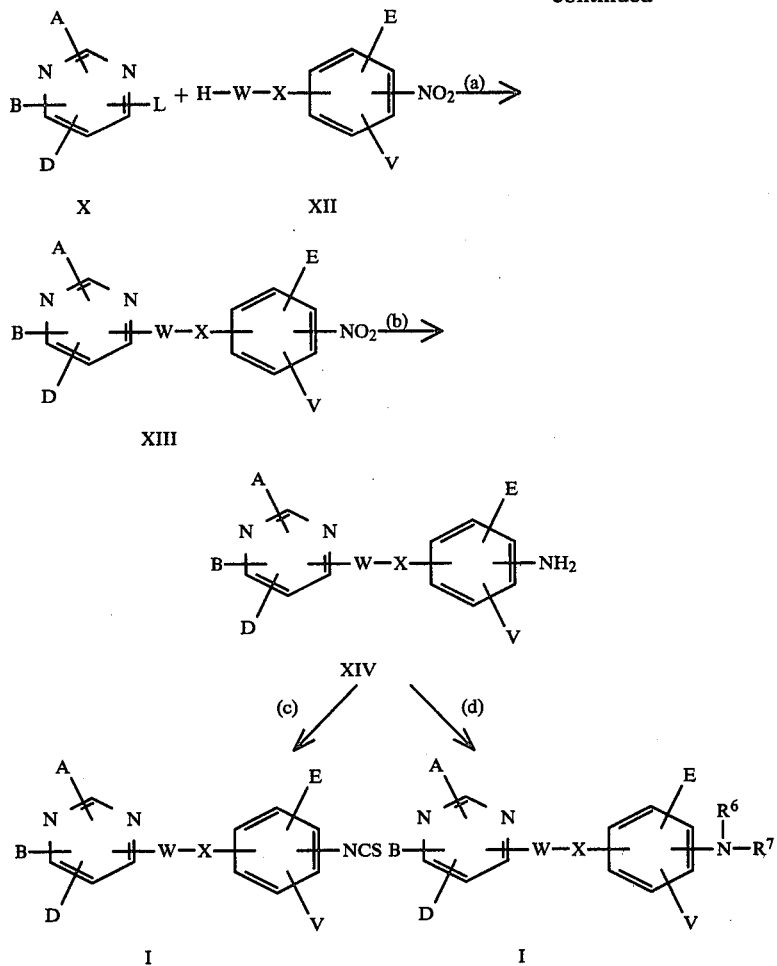
SCHEME 3
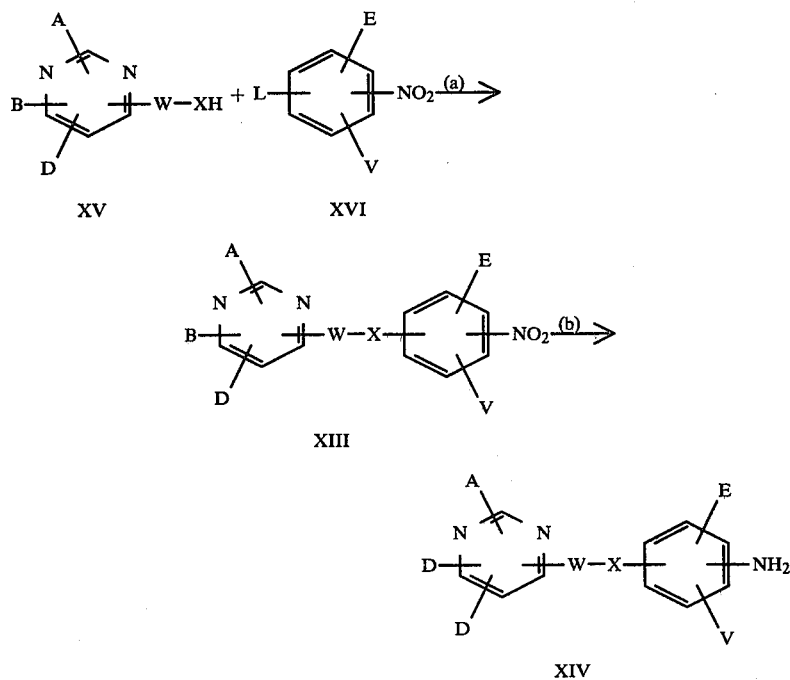
The reactions illustrated in SCHEME 1 and SCHEMES 2 and 3 Step (a) and outlined above prefera- The reaction conditions required to effect the reactions illustrated in SCHEME 1 and SCHEMES 2 and 3 Step (a) and outlined above vary according to the nature of the reactants, the alkaline material and the solvent used. In general, the reaction is facilitated by the application of heat and usually a reaction temperature in the range from 40° to 150° C. and a reaction time of between 0.5 and 20 hours is saticfactory. However, higher or lower reaction temperatures and/or shorter or longer reaction times may be used if desired.

Certain of the compounds of formula I which may be used in the process of the invention are novel compounds and in further embodiments the invention provide novel compounds, methods for the preparation thereof and compositions thereof. Examples of such novel compounds include compounds of the formula I wherein W is the group

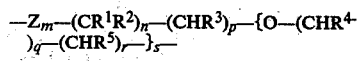

in which Z is oxygen or sulfur, $R^1$, $R^2$, $R^3$, $R^4$ and $R^5$ are independently chosen from hydrogen and lower alkyl, m is 0 or 1, n, p, q, r and s are independently 0 or an integer from 1 to 6 provided that m is 0 when n and p are both 0, s is 0 when q and r are both 0, and $n+p+s(q+r)$ is not greater than 12;

A, B, D, E, and V are independently chosen from the group consisting of hydrogen, halogen, nitro, amino, cyano, hydroxy, mercapto, thiocyano, carboxy, formyl, lower alkanoyl, (lower alkoxy)carbonyl, optionally substituted lower alkyl, optionally substituted lower alkoxy, optionally substituted lower alkenyl, optionally substituted aryl, optionally substituted aryloxy, optionally substituted lower alkylthio, lower alkanoylamino, lower alkylamino and lower di(lower alkyl)amino;

Z is chosen from isothiocyanate and $NR^6R^7$ wherein $R^6$ is chosen from hydrogen and lower alkyl and $R^7$ is chosen from hydrogen, optionally substituted lower alkyl, optionally substituted lower alkenyl and the group

in which Y is oxygen or sulfur and $R^8$ is optionally substituted lower alkyl or optionally substituted lower alkenyl; and X is oxygen or sulfur; or a salt thereof.

The process of the invention finds application in the treatment of warm-blooded animals to eradicate internal parasites of then *Fasciola spp.* such as, for example, *Fasciola hepatica* and *Fasciola gigantica* and *Haemonchus spp* such as, for example, *Haemonchus contortus.* The process of the invention is particularly useful in the treatment of warm-blooded animals such as sheep, cattle and goats to eradicate *Fascioal hepatica* (liver fluke) as, unlike most commercially available flukicides, the compounds of formual I are active against the immature as well as the mature forms of liver fluke.

In the process of the invention the compounds of formula I are preferably administered in the form of a composition. For effective treatment certain dosage levels are desired depending upon the compound employed, the type of animal to be treated and the particular helminth being combatted. In general, efficacy against fluke is achieved when the composition is administered in a single dose at dosage levels of from about 10 to 200 mg active ingredient/kg of animal body weight, and preferably from about 20 to 100 mg active ingredient per kg of animal body weight.

The compositions may be adminstered in a variety of ways, depending upon the particular animal employed, the type of anthelmintic treatment normally given to such an animal, the materials employed, and the particular helminths being combatted. It is preferred to adminster them in a single efficacious oral or parenteral dose at a time when fluke or nematode infection is apparent or suspected. They may be employed alone or in combination with other anthelmintics, parasiticides or antibacterals. The compounds may also be applied as a "pour on" formulation for dermal application. The amounts of the active anthelmintic ingredient in the composition, as well as the remaining constituents are varied according to the type of treatment to be employed, the host animal, and the particular parasitic disease being treated. In general, however, compositions containing a total weight percent of the active compound or compounds ranging from 0.001 to 95% will be suitable with the remainder being any suitable carrier or vehicle. Furthermore, the compositions should contain enough of the active ingredient to provide an effective dosage for the proper treatment of the parasitic disease.

A number of modes of treatment may be employed, and each to some extent determines the general nature of the composition. For example, the anthelmintic compositions may be administered to domesticated animals in single unit oral dosage form such as a tablet, bolus, capsule or drench; in a liquid form suitable for parenteral administration; or they may be compounded as feed premix to be later admixed with the animal's food.

When the compositions are to be solid unit dosage forms as in tablets, capsules, or boluses, the ingredients other than the acitve ingredient may be any other pharmaceutically acceptable vehicles convenient in the preparation of such forms, and preferably materials nutritionally suitable such as starch, lactose, talc, magnesium stearate, vegetable gums, and the like. Moreover when capsules are employed the active compound may be used in essentially undiluted form the only extraneous material being that of the capsule casing itself which may be hard or soft gelatin or any other pharmaceutically acceptable encapsulating material. When the dosage form is to be used for parenteral administration, the active material is suitably admixed with an acceptable base vehicle. In all of such forms, ie in tablets, boluses, capsule, and injectable formulations, the active compound conveniently ranges from about 5 to 80% by weight of the total composition.

When the unit dosage form is to be in the form of a drench, the active ingredient may be mixed with agents which will aid in the subsequent suspending of the active compound in water, such as bentonite, clays, water-soluble starch, cellulose derivatives, gums, surface active agents and the like to form a dry predrench composition added to water just before use. In the predrench formulation, in addition to the suspending agent, such ingredients as preservatives, antifoam compounds, and the like may be employed. Such a dry product may contain as much as 95% by weight of the active compound, the rest being contributed by the excipients. Preferably, the solid composition contains from 30% to 95% by weight of the active compound. Enough water should be added to the solid product to provide the proper dosage level within a convenient amount of liquid for a single oral dose. Liquid drench formulations containing from about 10 to 50 weight percent of dry ingredients will in general be suitable with the preferred range being from 15 to 30 weight percent. Where the compositions are intended to be used as feeds, feed compositions, or feed premixes, they will be mixed with suitable ingredients of an animal's nutrient ration. The solid orally-ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotics mycelia, soya grits, crushed limestone and the like are all suitable. The active compounds are intimately dispersed or admixed throughout the solid inert carrier by methods such as grinding, stirring, milling or tumbling. By selecting proper diluents and by altering the ratio of carrier to active ingredient, compositions of a desired concentration may be prepared. Feed supplement formulations containing from about 10 to 30% by weight of active ingredient are particularly suitable for addition to feeds. The active compound is normally dispersed or mixed uniformly in the diluent but in some instances may be adsorbed on the carrier.

These supplements are added to the finished animal feed in an amount adequate to give the final concentration of active ingredient desired for controlling or treating the helminth infection by way of the animal ration. Although the preferred level in feeds will depend on the particular compounds being employed, the active ingredients of this invention are normally fed at levels of 0.05–25% in the feed. As stated above, animals are preferably treated at a time when the infestation is apparent or suspected and the most preferred method for such treatment is via the single dose technique. Thus administration of medicated feed is not preferred but may certainly be employed. Similarly, the amounts of drug present in the feed may be reduced to levels in the order of 0.001% to 3.0 weight percent based on the weight of feed, and the medicated feed administered over prolonged periods. This would be in the nature of a preventive or prophylactic but again is not the mode of choice. Another method of administering the compositions of this invention to animals whose feeds are conveniently pelleted, such as sheep, is to incorporate them directly in the pellets. For instance, the compositions are readily incorporated in nutritionally adequate alfalfa pellets at levels of 2 to 110 grams per pound of pellets for therapeutic use, and at lower levels for example 80 to 1000 milligrams per pound for prophylactic use, and such pellets fed to the animals. The compositions may also optionally contain other drugs of veterinary utility. Veterinary drugs which may be present in the veterinary compositions of this invention depend upon the mode of administration of the said compositions, include for example, piperazine, 1-diethylcarbamyl-4-methylpiperazine, tetrachloroethylene, organic and inorganic arsenical compounds, tetramisole, 2-phenylbenzimidazole, thiabendazole, phenothiazine, mebendazole and pyrantel salts.

The compositions may be administered to the animal by parenteral dose and in a further aspect the invention provides a process for killing internal parasites or warm blooded animals which process comprises parenteral administration of an injectable composition comprising as active ingredient from 5 to 70% w/w, preferably 5 50% w/w, of a compound of the general formula I as hereinbefore defined in a pharmaceutically acceptable solvent carrier. The composition may be sterilized by methods known to those skilled in the art for the sterilization of injectable solutions such as, for example, ultra filtration or gamma radiation.

The compositions may also be administered by application to the skin of the animal and in yet a further aspect the invention provides a process for killing internal parasites or warm blooded animals which process comprises dermal application of liquid composition comprising as active ingredient from 1 to 70% w/w, preferably 1 to 10% w/w, of a compound of general formula I, as hereinbefore defined, dissolved or suspended in a pharmaceutically acceptable liquid carrier. Suitable liquid carriers include, for example, pharmaceutically acceptable hydrocarbons, ketones, esters, ethers, alcohols, amides, sulphones and sulphoxides.

The invention is now illustrated by, but by no means limited to, the following examples in which all parts are part by weight unless otherwise specified.

EXAMPLE 1

Preparation of
2-(4-Aminophenoxy)-5-chloropyrimidine (1)

A mixture of 5-chloro-2-methylsulfonylpyrimidine* (94 g), p-aminophenol (53 g), potassium carbonate (50 g) and methyl ethyl ketone (350 ml) was heated under reflux for a period of 3 hours. The mixture was filtered and the residue was washed with 2×200 ml of boiling acetone. Evaporation of the combined organic liquors left an orange oil. This readily dissolved in benzene and on standing the product crystallised and was collected by filtration and dried. Yield 80 g (74%), m.p. 125° C.
Budesinsky and J Vavrina, Coll. Czech. Chem. Comm. (1972), 37, 1721.

EXAMPLE 2

Preparation of
2-(4-Acetamidophenoxy)-5-chloropyrimidine (2)

2-(4-Aminophenoxy)-5-chloropyrimidine (20 g), was dissolved in acetic acid (100 ml), and acetic anhydride (20 ml) was added to the solution. After standing for a period of 5 minutes the solution was heated on a steam bath and hot water (100 ml) was slowly added. On cooling the product crystallised and was collected and dried. Yield 20 g, m.p. 202° C.

EXAMPLE 3

Preparation of
2-[2-(4-acetamidophenoxy)ethoxy]-5-chloropyrimidine
(4)

(a) A mixture of 4-acetamidophenol (200 g) and sodium methoxide (2 g) was heated under nitrogen, with stirring, to a temperature of 172° C. and ethylene oxide (68 g) was passed into the stirred melt at a rate sufficient to maintain the temperature of the reaction mixture in the range from 170° to 180° C. On completion of the addition the mixture was cooled and diluted with a mixture of ethyl acetate (600 ml) and acetic acid (2 ml). 2-(4-Acetamidophenoxy)ethanol (180 g; 77%) crystallised spontaneously from the mixture and was collected by filtration and dried (m.p. 120° C.; B N Katrak, J. Ind. Chem. Soc., 13, 334 (1936) reports m.p. 116°–117° C.).

(b) A mixture of 2-(4-acetamidophenoxy)ethanol (25 g), granular sodium hydride (3.1 g) and dry tetrahydrofuran (250 ml) was heated under reflux for a period of 2 hours. 2,5-Dichloropyrimidine* (19 g) was added and the mixture was heated under reflux for a further 8 hours. The solvent was removed by distillation under reduced pressure, water was added and the crystalline product was collected and dried to give 2-[2-(4-acetamidophenoxy)ethoxy]-5-chloropyrimidine (35 g), m.p. 160° C.

*J. P. English et al, J. Amer. Chem. Soc., 68, 1039 (1946).

EXAMPLE 4

Preparation of 2-{2-[2-(4-acetamidophenoxy)ethoxy]-ethoxy}-5-chloropyrimidine (5)

(a) 2-[2-(4-Acetamidophenoxy)ethoxy]ethanol was prepared from 4-acetamidophenol (200 g) and ethylene oxide (136 g) following essentially the same procedure as that described in Example 3 part a). The compound was purified by fractional crystallisation from ethyl acetate, m.p. 94° C.

(b) 2-[2-(4-Acetamidophenoxy)ethoxy]ethanol (9 g) was dissolved in dry dimethylsulfoxide (60 ml) and granular sodium hydride (0.9 g) was added portionwise to the solution. 2,5-Dichloropyrimidine (5.6 g) was slowly added to the cooled stirred solution and on completion of the addition the mixture was stirred at room temperature for 1 hour. The mixture was poured into water (200 ml) and the solid was collected by filtration. The product was recrystallised from ethanol/water to give 2-{2-[2(4-acetamidophenoxy)ethoxy]ethoxy}-5-chloropyrimidine (8.4 g), m.p. 110° C.

EXAMPLE 5

The compounds numbered from 4 to 11 of formula I listed in Table 1 below prepared from the appropriate starting materials following essentially the same procedures described in the preceding Examples.

Methods 1, 2, 3 and 4b refer to the procedures of Examples 1, 2, 3 and 4 part b) respectively.

TABLE 1

B—[pyrimidine]—W—O—[phenyl]—NHR$^7$

| Compound No | Method | Substituents B | W | R$^7$ | MP °C. |
|---|---|---|---|---|---|
| 1 | 1 | Cl | — | H | 125 |
| 2 | 2 | Cl | — | CH$_3$CO | 202 |
| 3 | 1 | Br | — | H | 101 |
| 4 | 3 | Cl | OCH$_2$CH$_2$ | CH$_3$CO | 160 |
| 5 | 4 | Cl | (OCH$_2$CH$_2$)$_2$ | CH$_3$CO | 110 |
| 6 | 4(b) | Cl | O(CH$_2$)$_3$ | CH$_3$CO | 120 |
| 7 | 4(b) | Br | O(CH$_2$)$_3$ | CH$_3$CO | 128 |
| 8 | 4(b) | CF$_3$ | O(CH$_2$)$_3$ | CH$_3$CO | 130 |
| 9 | 4(b) | CH$_3$ | O(CH$_2$)$_3$ | CH$_3$CO | 135 |
| 10 | 4(b) | I | O(CH$_2$)$_3$ | CH$_3$CO | 140 |
| 11 | 4(b) | Cl | O(CH$_2$)$_4$ | CH$_3$CO | 141–2 |

EXAMPLE 6

Preparation of 4-(5-chloro-2-pyrimidyloxy)phenylisothiocyanate (12)

A solution of 2-(4-aminophenoxy)-5-chloropyrimidine (11 g) was dissolved in dichloromethane (35 ml) and added dropwise to a vigorously stirred mixture of thiophosgene (5.75 g) and water (50 ml). The mixture was stirred for two hours and ethyl acetate (100 ml) added. After filtration of the reaction mixture the liquid organic phase was separated, dried and the solvent removed by evaporation. The residue was crystallized from dichloromethane/light petroleum to yield 10 g of (1) with mp 148° C.

EXAMPLE 7

Preparation of 4-(5-chloro-2-pyrimidyloxy)phenylisothiocyanate (12)

(a) To a stirred slurry of p-aminophenol (10 g) and water (80 ml) thiophosegene (10.5 g) was added dropwise. The suspension was stirred for a further 2 hours, then extracted with ether (2x). The extract was washed in turn with 5% HCl, 5% NaHCO$_3$, water brine and was dried over magnesium sulphate. The dried extract was flash distilled and the fraction was collected at 110°–112° C. and 0.1–0.05 mm to give p-hydroxyphenylisothiocyanate as a colourless solid (11.9 g, 86%) m.p. /50° C.

(b) A mixture of p-hydroxyphenylisothiocyanate (10 g), 2,5 dichloropyrimidine (10 g), potassium carbonate (8 g) and methyl ethyl ketone was stirred and refluxed for 24 hrs. The suspension was allowed to cool, then filtered and filtrate washed exhaustively with ethyl acetate. The two fractions were combined and washed in turn with 5% HCl, 5% NaOH, H$_2$O, brine, dried with magnesium sulphate and evaporated under reduced pressure. Recrystallization from ethanol gave (I) (12.5 g, 70%) m.p. 148° C.

EXAMPLE 8

Compositions suitable for use as experimental aqueous oral drenches were prepared in the following general manner. A mixture of the required amount of active ingredient was mixed with 40 ml of an aqueous 0.25% w/w solution of "Lubrol E" ("Lubrol E" is a Trade Mark for an octylphenol ethoxylate). The mixture was ballmilled for 30 minutes and the resultant suspension was used as an aqueous drench.

EXAMPLE 9

Compositions suitable for use as experimental injectable solutions were prepared by formulating the compounds directly as solutions, or indirectly as solutions of their salts either in water or in a mixture of water and ethylene glycol or water and a polyethylene glycol (PEG200).

EXAMPLE 10

Compositions prepared by the method of Example 6 were used as a single dose to test sheep infected with sheep liver fluke (Fasciola hepatica). The number of liver fluke eggs in the faeces was measured at the time of treatment and at selected intervals up to 14 days after treatment. The sheep were killed and the number of adult fluke in the liver counted. The active ingredient in each composition, the does rate employed and the results of treatment of a sheep with that composition are given in the Table 2 below. The compositions were administered by oral drenching.

TABLE 2

FLUKICIDAL ACTIVITY OF COMPOSITIONS COMPRISING AS ACTIVE INGREDIENT A COMPOUND OF FORMULA I

| Compound No | DOSE RATE (mg/kg) | FAECAL EGG COUNT eggs/g faeces (day) | POST MORTEM no of adult fluke |
|---|---|---|---|
| 1 | 72 | 1000(0), 0(7), 0(14) | 0 |

TABLE 2-continued
FLUKICIDAL ACTIVITY OF COMPOSITIONS COMPRISING AS ACTIVE INGREDIENT A COMPOUND OF FORMULA I

| Compound No | DOSE RATE (mg/kg) | FAECAL EGG COUNT eggs/g faeces (day) | POST MORTEM no of adult fluke |
|---|---|---|---|
| 1 | 50 | 100(0), 0(7), 0(14) | 0 |
| 1 | 35 | 190(0), 90(7), 0(14) | 0 |
| 2 | 50 | 260(0), 10(7), 0(14) | 0 |
| 2 | 35 | 390(0), 10(7), 0(14) | 0 |
| 4 | 85 | 130(0), 0(7), 0(14) | 0 |
| 4 | 60 | 130(0), 0(7), 30(14) | 2 |
| 5 | 100 | 240(0), 0(7), 0(14) | 0 |
| 5 | 75 | 190(0), 10(7), 0(14) | 5 |
| 6 | 50 | 400(0), 70(7), 50(14) | 0 |
| 6 | 35 | 200(0), 60(7), 0(14) | 0 |
| 7 | 100 | 1100(0), 0(7), 0(14) | 0 |
| 8 | 50 | 280(0), 0(7), 0(14) | 0 |
| 9 | 100 | 400(0), 40(7), 20(14) | 0 |
| 10 | 100 | 520(0), 0(7), 0(14) | 0 |
| 11 | 100 | 250(0), 60(7), 20(14) | 0 |
| 11 | 50 | 560(0), 0(7), 0(14) | 1 |
| 12 | 50 | 200(0), 0(7), 0(14) | 0 |

EXAMPLE 11

The minimum effective concentration of compounds of formula I against live Fasciola hepatica was tested by the direct application of the test compound, in solution, to live Fasciola hepatica in Hedon-Fleig medium. The results are given in Table 3 where the minimum effective concentration (minimum concentration required to kill Fasciola hepatica) was assessed 24 hours after treatment with the test compound.

TABLE 3

| COMPOUND NO | MINIMUM EFFECTIVE CONCENTRATION (parts per million) |
|---|---|
| 1 | 5 |
| 2 | 1 |

EXAMPLE 12

Compositions prepared by the method of Example 6 were tested for their activity against immature Fasciola hepatica by administering a single dose of the composition to sheep which had been experimentally infected by treatment with metacercariae from one to nine weeks earlier. Approximately ten weeks after infection the sheep were slaughtered and the number of fluke in the liver counted.

The active ingredient employed in each composition, the dose rate employed, the age of the immature Fasciola hepatica at the time of dosing, and the post mortem results are given in Table 4 below. the compositions were administered by oral drenching.

TABLE 4
ACTIVITY AGAINST IMMATURE (1 TO 9 WEEKS OLD) FASCIOLA HEPATICA OF COMPOSITIONS COMPRISING AS ACTIVE INGREDIENT A COMOUND OF FORMULA I

| Compound No | DOSE RATE (mg/kg) | Age of fluke (weeks) | POST MORTEM No of adult fluke (mean) | Untreated Controls | % Control (mean) |
|---|---|---|---|---|---|
| 1 | 25 | 1 | 0 | 21.5 | 100 |
| 1 | 25 | 3 | 0.33 | 21.5 | 98.5 |
| 1 | 25 | 4 | 0 | 21.5 | 98.5 |
| 1 | 37.5 | 1 | 0 | 21.5 | 100 |

TABLE 4-continued
ACTIVITY AGAINST IMMATURE (1 TO 9 WEEKS OLD) FASCIOLA HEPATICA OF COMPOSITIONS COMPRISING AS ACTIVE INGREDIENT A COMOUND OF FORMULA I

| Compound No | DOSE RATE (mg/kg) | Age of fluke (weeks) | POST MORTEM No of adult fluke (mean) | Untreated Controls | % Control (mean) |
|---|---|---|---|---|---|
| 1 | 37.5 | 3 | 0 | 21.5 | 100 |
| 1 | 37.5 | 4 | 0 | 21.5 | 100 |
| 1 | 50 | 1 | 0 | 21.5 | 100 |
| 1 | 50 | 3 | 0 | 21.5 | 100 |
| 1 | 50 | 4 | 0 | 21.5 | 100 |
| 1 | 50 | 4 | 0 | 77 | 100 |
| 2 | 25 | 2 | 0.33 | 21.5 | 98.5 |
| 2 | 50 | 2 | 0 | 21.5 | 100 |
| 2 | 50 | 4 | 0 | 21.5 | 100 |
| 4 | 100 | 4 | 0 | 77 | 100 |
| 12 | 50 | 4 | 0 | 77 | 100 |
| 12 | 50 | 9 | 0 | 62.5 | 100 |
| 12 | 37.5 | 9 | 0.5 | 62.5 | 99.2 |

We claim:

1. A compound or a pharmaceutically acceptable salt thereof of the formula

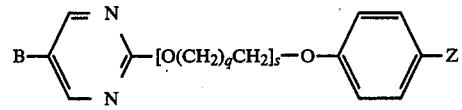

wherein B is halogen or trifluoromethyl, Z is isothiocyano or NHR[7]

wherein R[7] is hydrogen or acetyl, s is an integer from 1 to 2, q is an integer from 1 to 3, with the proviso that when s is 2, q is 1.

2. A compound or a pharmaceutically acceptable salt thereof of the formula

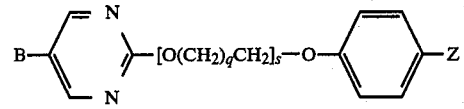

wherein B is halogen or trifluoromethyl, Z is isothiocyano, s is an integer from 0 to 2, q is an integer from 1 to 3, with the proviso that when s is 2, q is 1.

3. A compound or a pharmaceutically acceptable salt thereof of the formula

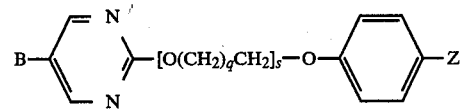

wherein B is halogen or trifluoromethyl, Z is NHR[7] wherein R[7] is acetyl, s is an integer from 0 to 2, q is an integer from 1 to 3, with the proviso that when s is 2, q is 1.

4. A compound or a pharmaceutically acceptable salt thereof of the formula

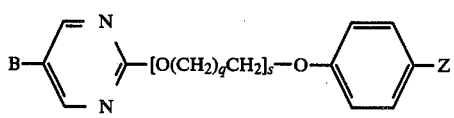

wherein B is trifluoromethyl, Z is isothiocyano or NHR[7]

wherein R[7] is hydrogen or acetyl, s is an integer from 0 to 2, q is an integer from 1 to 3, with the proviso that when s is 2, q is 1.

5. A compound selected from the group consisting of 2-{2-(4-acetamidophenoxy)ethoxy}-5-chloropyrimidine, 2-{2-[2-(4-acetamidophenoxy)ethoxy]ethoxy}-5-chloropyrimdine, 2-{3-(4-acetamidophenoxy)propoxy}-5-chloropyrimidine, 2-{3-(4-acetamidophenoxy)propoxy}-5-bromopyrimidine, 2-{3-(4-acetamidophenoxy)propoxy}-5-trifluormethylpyrimidine, 2-{3-(4-acetamidophenoxy)propoxy}-5-methylpyrimidine, 2-{3-(4-acetamidophenoxy)propoxy}-5-iodopyrimidine and 2-{4-(4-acetamidophenoxy)butoxy}-5-chloropyrimidine.

6. A process for killing internal parasites of warm-blooded animals which process comprises treating the infected animal with an effective amount of a composition comprising as active ingredient a compound or pharmaceutically acceptable salt thereof of the formula:

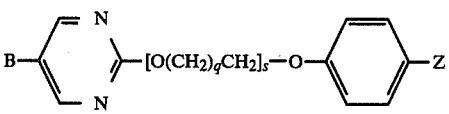

wherein B is halogen or trifluoromethyl, Z is isothiocyano or NHR[7]

wherein R[7] is hydrogen or acetyl, s is an integer from 0 to 2, q is an integer from 1 to 3, with the proviso that when s is 2, q is 1.

7. A process for killing internal parasites of warm-blooded animals which process comprises treating the infected animal with an effective amount of a composition comprising as active ingredient a compound according to claim 1.

8. A process according to claim 7 wherein the internal parasite is a trematode of the *Fasciola sp* or a nematode of the *Haemonchus sp.*

9. A process according to claim 7 wherein the internal parasite is the live fluke (*Fasciola hepatica*).

10. A process according to claim 7 wherein the composition comprises from 10 to 200 mg of active ingredient per kilogram of animal body weight.

11. A process according to claim 7 wherein the composition, in the form of a sterile injectable composition, is adminstered by injection.

12. A process according to claim 7 wherein the composition, in liquid form, is administered by topical application.

13. A process according to claim 7 wherein the composition is administered by oral drench.

14. A composition comprising as active agent a compound according to claim 1 and an inert carrier therefor.

15. A sterile injectable composition comprising as active ingredient 5 to 70% w/w of a compound of general formula I as defined according to claim 1 and a pharmaceutically acceptable solvent carrier therefor.

16. A liquid composition comprising as active ingredient from 10 to 50% w/w of a compound according to claim 1 and a pharmaceutically acceptable liquid carrier.

* * * * *